US012611235B2

(12) United States Patent
Mauldin et al.

(10) Patent No.: US 12,611,235 B2
(45) Date of Patent: Apr. 28, 2026

(54) INTRAMEDULLARY NAIL WITH AUTOMATIC DYNAMIZATION AND CONTINUOUS COMPRESSION

(71) Applicant: GLW, Inc., Englewood Cliffs, NJ (US)

(72) Inventors: Garret Mauldin, Erie, CO (US); Yash Dalal, Englewood Cliffs, NJ (US); Axel Cremer, Fahrenkrug (DE)

(73) Assignee: GLW, Inc., Englewood Cliffs, NJ (US)

( * ) Notice: Subject to any disclaimer, the term of this patent is extended or adjusted under 35 U.S.C. 154(b) by 0 days.

(21) Appl. No.: 18/590,184

(22) Filed: Feb. 28, 2024

(65) Prior Publication Data

US 2024/0285317 A1     Aug. 29, 2024

Related U.S. Application Data

(60) Provisional application No. 63/448,828, filed on Feb. 28, 2023.

(51) Int. Cl.
*A61B 17/72* (2006.01)
(52) U.S. Cl.
CPC ................................. *A61B 17/7233* (2013.01)
(58) Field of Classification Search
CPC .. A61B 17/72; A61B 17/7233; A61B 17/7225
See application file for complete search history.

(56) References Cited

U.S. PATENT DOCUMENTS 4,237,875 A * 12/1980 Termanini .......... A61B 17/7266
606/63
5,074,882 A 12/1991 Grammont et al.
(Continued)

FOREIGN PATENT DOCUMENTS

EP        1379186 B1    5/2009
EP        1557131 B1    3/2010
(Continued)

OTHER PUBLICATIONS

McCormick et al., "Biomechanical investigation of a novel ratcheting arthrodesis nail", Journal of Orthopaedic Surgery and Research, 2010, vol. 5, No. 74, pp. 1-6.
(Continued)

*Primary Examiner* — Jacqueline T Johanas
(74) *Attorney, Agent, or Firm* — MacMillan, Sobanski & Todd, LLC

(57) ABSTRACT

An intramedullary nail comprises an elongate body having a distal end, a proximal end, a distal portion, a proximal portion, an inner surface, and an outer surface, the distal portion disposed between the distal end and the proximal portion, the proximal portion disposed between the distal portion and the proximal end, the inner surface defining a first lumen extending through the distal portion and a second lumen extending through the proximal portion, the inner surface including a receiving surface; a first movable member disposed within the first lumen, the first movable member having a first movable member outer surface; a first peripheral projection disposed on the first movable member outer surface; a second movable member disposed within the second lumen, the second movable member having a second movable member outer surface; and a second peripheral projection disposed on the second movable member outer surface.

16 Claims, 13 Drawing Sheets

(56) References Cited

U.S. PATENT DOCUMENTS

| | | | | |
|---|---|---|---|---|
| 5,626,581 | A * | 5/1997 | Staehlin | A61B 17/7216 606/53 |
| 6,034,295 | A * | 3/2000 | Rehberg | A61B 17/72 607/51 |
| 6,221,074 | B1 * | 4/2001 | Cole | A61B 17/72 606/62 |
| 6,575,973 | B1 * | 6/2003 | Shekalim | A61B 17/7266 606/68 |
| 6,808,527 | B2 | 10/2004 | Lower et al. | |
| 6,942,668 | B2 | 9/2005 | Padget et al. | |
| 7,008,428 | B2 | 3/2006 | Cachia et al. | |
| 7,947,043 | B2 | 5/2011 | Mutchler | |
| 8,328,807 | B2 | 12/2012 | Brigido | |
| 8,915,917 | B2 | 12/2014 | Doherty et al. | |
| 9,339,312 | B2 | 5/2016 | Doherty et al. | |
| 9,393,119 | B2 | 7/2016 | Pool et al. | |
| 9,532,817 | B2 | 1/2017 | Overes | |
| 10,610,368 | B2 | 4/2020 | Ehmke | |
| 10,729,475 | B2 | 8/2020 | Childs | |
| 2004/0127898 | A1 * | 7/2004 | Adam | A61B 17/72 606/64 |
| 2006/0129247 | A1 * | 6/2006 | Brown | A61F 2/3607 606/62 |
| 2006/0229617 | A1 * | 10/2006 | Meller | A61F 2/3662 606/62 |
| 2007/0270855 | A1 * | 11/2007 | Partin | A61B 17/863 606/279 |
| 2011/0087227 | A1 * | 4/2011 | Mazur | A61B 17/7266 606/62 |
| 2012/0130370 | A1 | 5/2012 | Kinmon | |
| 2012/0136356 | A1 * | 5/2012 | Doherty | A61B 17/7225 606/62 |
| 2015/0127002 | A1 | 5/2015 | Doherty et al. | |
| 2017/0296241 | A1 * | 10/2017 | Garlock | A61B 17/7241 |
| 2017/0360489 | A1 * | 12/2017 | Palmer | A61B 17/863 |
| 2021/0259748 | A1 * | 8/2021 | Mullaney | A61B 17/7216 |
| 2021/0386463 | A1 * | 12/2021 | Majors | A61B 17/7291 |
| 2022/0304730 | A1 * | 9/2022 | Beckett | A61B 17/7225 |

FOREIGN PATENT DOCUMENTS

| | | | | | |
|---|---|---|---|---|---|
| EP | | 2464300 | B1 * | 8/2014 | A61B 17/7225 |
| FR | | 2726460 | A1 | 5/1996 | |
| WO | WO-9738641 | | A1 * | 10/1997 | A61B 17/7216 |
| WO | WO-2011018778 | | A1 * | 2/2011 | A61B 17/7225 |
| WO | WO-2016044728 | | A1 * | 3/2016 | A61B 17/7225 |

OTHER PUBLICATIONS

International Search Report and Written Opinion, Application No. PCT/US2024/017667, dated Jul. 26, 2024.

* cited by examiner

INTRAMEDULLARY NAIL WITH AUTOMATIC DYNAMIZATION AND CONTINUOUS COMPRESSION

CROSS-REFERENCE TO RELATED APPLICATION

This application claims the benefit of U.S. Provisional Application No. 63/448,828, filed on Feb. 28, 2023, which is incorporated by reference into this disclosure in its entirety.

FIELD

The disclosure relates to the field of medical devices. More particularly, the disclosure relates to intramedullary nails useful in the repair of fractured bones.

BACKGROUND

Intramedullary nails, also referred to as intramedullary rods or bone nails, are implantable medical devices that are commonly used for fracture stabilization and fixation. Intramedullary nails are often cannulated to allow them to be placed over a wire to guide their positioning and to align bone fragments sought to be stabilized. Intramedullary nails often include structural features, such as through passageways, to facilitate placement of locking screws used to attach parts of the fractured bone to the nail or to ensure a reliable fixation of the nail in the intramedullary canal. Typically, locking screws are attached through both sides of the nail and the bone.

When first implanting an intramedullary nail, the fracture or fusion site needs to be reduced to compress bone portions together to promote proper healing of the bone. This reduction can be accomplished in multiple ways. For example, after fixing one end of an intramedullary nail in a bone, a mallet can be used strike the opposite end of the nail to compress the joint or fracture. A screw is typically inserted through an opening near the end of the nail struck with the mallet to maintain the compression. In another approach to achieving reduction, tension on an internal structural element inside the nail is released after the nail is fixed in place, providing desired compression to the joint or fracture site. This approach provides continuous compression to the fracture site following placement of the intramedullary nail.

Dynamic compression, which allows one end of the nail to move axially relative to the other end following placement, may be beneficial in some clinical situations. Dynamization allows weight bearing on the bone to move one end of the intramedullary nail axially relatively to the other end of the nail, which may stimulate osseous growth and promote bone healing.

The amount by which a conventional intramedullary nail moves through dynamization is not controlled; dynamization of these nails is a binary situation. Excess movement may overcome any potential benefit of the approach, leading many providers to avoid it altogether.

A need exists, therefore, for improved intramedullary nails.

BRIEF SUMMARY OF SELECTED EXAMPLES

Various example intramedullary nails are described.

An example intramedullary nail comprises an elongate body having a distal end, a proximal end, a distal portion, a proximal portion, an inner surface, and an outer surface, the distal portion disposed between the distal end and the proximal portion, the proximal portion disposed between the distal portion and the proximal end, the inner surface defining a first lumen extending through the distal portion and a second lumen extending through the proximal portion, the inner surface including a receiving surface; a first movable member disposed within the first lumen, the first movable member having a first movable member outer surface; a first peripheral projection disposed on the first movable member outer surface; a second movable member disposed within the second lumen, the second movable member having a second movable member outer surface; and a second peripheral projection disposed on the second movable member outer surface.

Another example intramedullary nail comprises an elongate body having a distal end, a proximal end, an inner surface, and an outer surface, the inner surface defining a lumen between the proximal end and the distal end, the inner surface having a receiving surface; a movable member disposed within the lumen, the movable member having a movable member outer surface; and a peripheral projection disposed on the movable member outer surface.

Another example intramedullary nail comprises an elongate body having a distal end, a proximal end, an inner surface, and an outer surface, the inner surface defining a lumen between the proximal end and the distal end; a movable member disposed within the lumen, the movable member having a movable member outer surface; and elastic compression members disposed on the movable member outer surface, each of the elastic compression members having a raised side, and the elastic compression members arranged in alternating orientations.

Another example intramedullary nail comprises an elongate body having a distal end, a proximal end, an inner surface, and an outer surface, the inner surface defining a lumen between the proximal end and the distal end; a movable member disposed within the lumen, the movable member having a movable member outer surface and a locking portion, the locking portion including an extension with a ledge; and a slot formed in the proximal end, wherein the locking portion has a locked position and an unlocked position, the locked position is when the ledge is disposed through the slot and misaligned with the slot, and the unlocked position is when the ledge is aligned with the slot and disposed in the elongate body. The locked position prevents dynamization during implantation of the intramedullary nail, which is critical to prevent undesirable dynamization while the intramedullary nail is hammered into position during implantation.

Another example intramedullary nail comprises an elongate body having a distal end, a proximal end, a distal portion, a proximal portion, an inner surface, and an outer surface, the distal portion disposed between the distal end and the proximal portion, the proximal portion disposed between the distal portion and the proximal end, the inner surface defining a first lumen extending through the distal portion and a second lumen extending through the proximal portion, the inner surface including a receiving surface having stepped grooves; a first movable member disposed within the first lumen, the first movable member having a first movable member outer surface; elastic compression members disposed on the first movable member outer surface, each of the elastic compression members having a raised side, and the elastic compression members arranged in alternating orientations; a second movable member disposed within the second lumen, the second movable member having a second movable member outer surface; and a wedged split sleeve disposed on the second movable member outer surface, the wedged split sleeve having ridges.

Another example intramedullary nail comprises an elongate body having a distal end, a proximal end, a distal portion, a proximal portion, an inner surface, and an outer surface, the distal portion disposed between the distal end and the proximal portion, the proximal portion disposed between the distal portion and the proximal end, the inner surface defining a first lumen extending through the distal portion and a second lumen extending through the proximal portion, the inner surface including a receiving surface having stepped grooves; a first movable member disposed within the first lumen, the first movable member having a first movable member outer surface; elastic compression members, such as elastic projections, disposed on the first movable member outer surface, each of the elastic compression members having a raised side, and the elastic compression members arranged in alternating orientations; a second movable member disposed within the second lumen, the second movable member having a second movable member outer surface and a locking portion, the locking portion including an extension with a ledge; and a wedged split sleeve disposed on the second movable member outer surface, the wedged split sleeve having ridges; and a slot formed in the proximal end, wherein the locking portion has a locked position and an unlocked position, the locked position is when the ledge is disposed through the slot and misaligned with the slot, and the unlocked position is when the ledge is aligned with the slot and disposed in the elongate body.

Additional understanding of the inventive intramedullary nails can be obtained by reviewing the detailed description of selected examples, below, and the referenced drawings.

DETAILED DESCRIPTION OF SELECTED EXAMPLES

The following detailed description and the appended drawings describe and illustrate various example intramedullary nails. The description and illustration of these examples enable one skilled in the art to make and use examples of the intramedullary nails. They do not limit the scope of the claims in any manner.

Figures 1, 2:
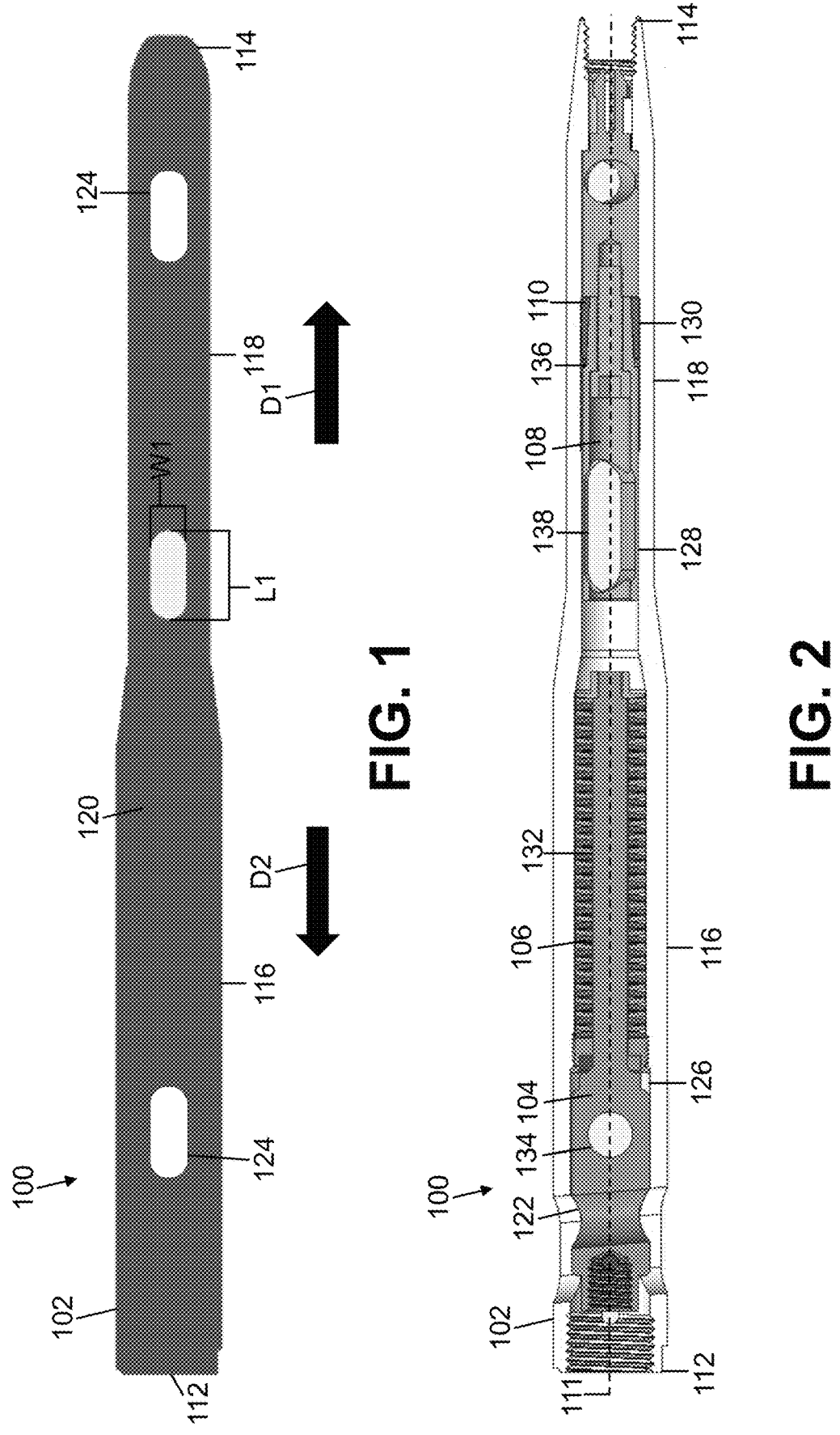
FIG. 1 is a top view of an example intramedullary nail.
FIG. 2 is a sectional view of the intramedullary nail illustrated in FIG. 1.

FIGS. 1 and 2 illustrate a first example intramedullary nail 100. The intramedullary nail 100 has an elongate body 102, a first movable member 104, a first elastic compression member as a peripheral projection 106, a second movable member 108, and a second elastic compression member as a peripheral projection 110. In the illustrated example, the elongate body 102 is disposed along a longitudinal axis 111. The elongate body 102 has a distal end 112, a proximal end 114, a distal portion 116, a proximal portion 118, an outer surface 120, and an inner surface 122. The distal end 112 is opposite to the proximal end 114. In certain embodiments, the proximal end 114 is defined as the end of the intramedullary nail 100 that is first inserted into a bone. However, in certain configurations, the proximal end 114 and the distal end 112 may be swapped. The distal portion 116 is adjacent to the distal end 112. The distal portion 116 is disposed between the distal end 112 and the proximal portion 118. The proximal portion 118 is adjacent to the proximal end 114. The proximal portion 118 is disposed between the distal portion 116 and the proximal end 114.

The outer surface 120 and inner surface 122 can define one or more elongate body screw passageways 124 formed through the elongate body 102. The elongate body screw passageway 124 can be adapted to receive a screw to lock the elongate body 102 into position in a bone or to lock internal components of the elongate body 102 into position. In the illustrated example, the elongate body screw passageway 124 has a slotted shape. Other shapes may also be selected. The elongate body screw passageway 124 can have a length L1 and a width W1 (shown in FIG. 1), whereby the length L1 is greater than the width. In certain examples, the length L1 is between about 0 mm to about 10 mm, between about 3 mm to about 8 mm, or more about 6 mm. As will be described below, the length L1 of the elongate body screw passageway 124 can directly correlate to the distance the first movable member 104 and/or the second movable member 108 can travel. As such, the length L1 of the elongate body screw passageway 124 can be scaled based on the desired travel distance.

As shown in the illustrated example in FIG. 2, the inner surface 122 defines a first lumen 126, a second lumen 128, and a receiving surface 130. The first lumen 126 can extend through the distal portion 116, e.g., from the distal end 112 towards the proximal portion 118. The second lumen 128 can extend through the proximal portion 118, e.g., from the distal portion 116 towards the distal end 112. In certain embodiments, the inner surface 122 defines a main lumen, and the first lumen 126 and the second lumen 128 are part of the main lumen. In the illustrated example, the receiving surface 130 is defined in the second lumen 128. However, in certain configurations, the receiving surface 130 can be defined in the first lumen 126. Aspects of the receiving surface 130 will be discussed later with respect to the second movable member 108.

In the illustrated example, the first movable member 104 is disposed within the first lumen 126. The first movable member 104 can be adapted to be selectively movable along the longitudinal axis 111 in the first lumen 126 (or the main lumen in certain embodiments). The first movable member 104 has a first movable member outer surface 132. The first movable member 104 can also define one or more first member screw passageways 134. The first member screw passageway 134 can be adapted to align with one of the elongate body screw passageways 124 and receive a screw to restrict the movement of the first movable member 104 by the length L1 of the first member screw passageway 134.

The first peripheral projection 106 is disposed on the first movable member outer surface 132. The first peripheral projection 106 can be adapted to maintain a compression force in a first direction D1 (towards the proximal end 114 of the elongate body 102). In particular, when the first movable member 104 travels in the first direction D1 and is locked into a position (such as a screw disposed through the first member screw passageway 134), the first peripheral projection 106 can maintain a compression force in the first direction D1. This can provide for continuous compression, which can be advantageous as continuously compressing the fracture or fusion site can facilitate proper healing of the bone.

In the illustrated example, the second movable member 108 is disposed within the second lumen 128. The second movable member 108 can be adapted to be selectively movable along the longitudinal axis 111 in the second lumen 128 (or the main lumen in certain embodiments). The second movable member 108 has a second movable member outer surface 136. The second movable member 108 can also define one or more second member screw passageways 138. The second member screw passageway 138 can be adapted to align with one of the elongate body screw passageways 124 and receive a screw to restrict the movement of the second movable member 108 by the length L1 of the elongate body screw passageway 124. In certain embodiments, the elongate body 102 further comprises a main movable member, and the first movable member 104 and the second movable member 108 are part of the main movable member.

The second peripheral projection 110 is disposed on the second movable member outer surface 136. The second peripheral projection 110 can be adapted to cooperate with the receiving surface 130 to enable the second movable member 108 to travel in the first direction D1 while militating against or preventing the second movable member 108 from traveling in a second direction D2 opposite to the first direction D1. Specifically, when a force, such as a force from weight bearing or walking, causes the second movable member 108 to travel through the receiving surface 130 in the first direction D1, the receiving surface 130 allows the second peripheral projection 110 to pass through the receiving surface 130. If a force attempts to move the second movable member 108 back in the second direction D2, the receiving surface 130 militates against or prevents the second movable member 108 from moving in the second direction D2. This can provide controlled automatic dynamization, which enables the second movable member 108 to automatically move towards the first direction D1 from forces that occur during weight bearing or walking. Desirably, automatic dynamization enables for outpatient and timely compressing of the joint and fracture while the bone is reabsorbing, actuated by the patient's normal ambulation through body weight. The compression of the joint and fracture, while the bone is reabsorbing, can enable proper bone contact for faster healing, and importantly without surgical intervention. During surgical implantation of the intramedullary nail 100, this same feature of dynamization can also be used for manually compression a joint by using forceful impacts with a mallet on the distal end of the nail, thereby moving the movable member 108.

Figures 3, 4, 5:
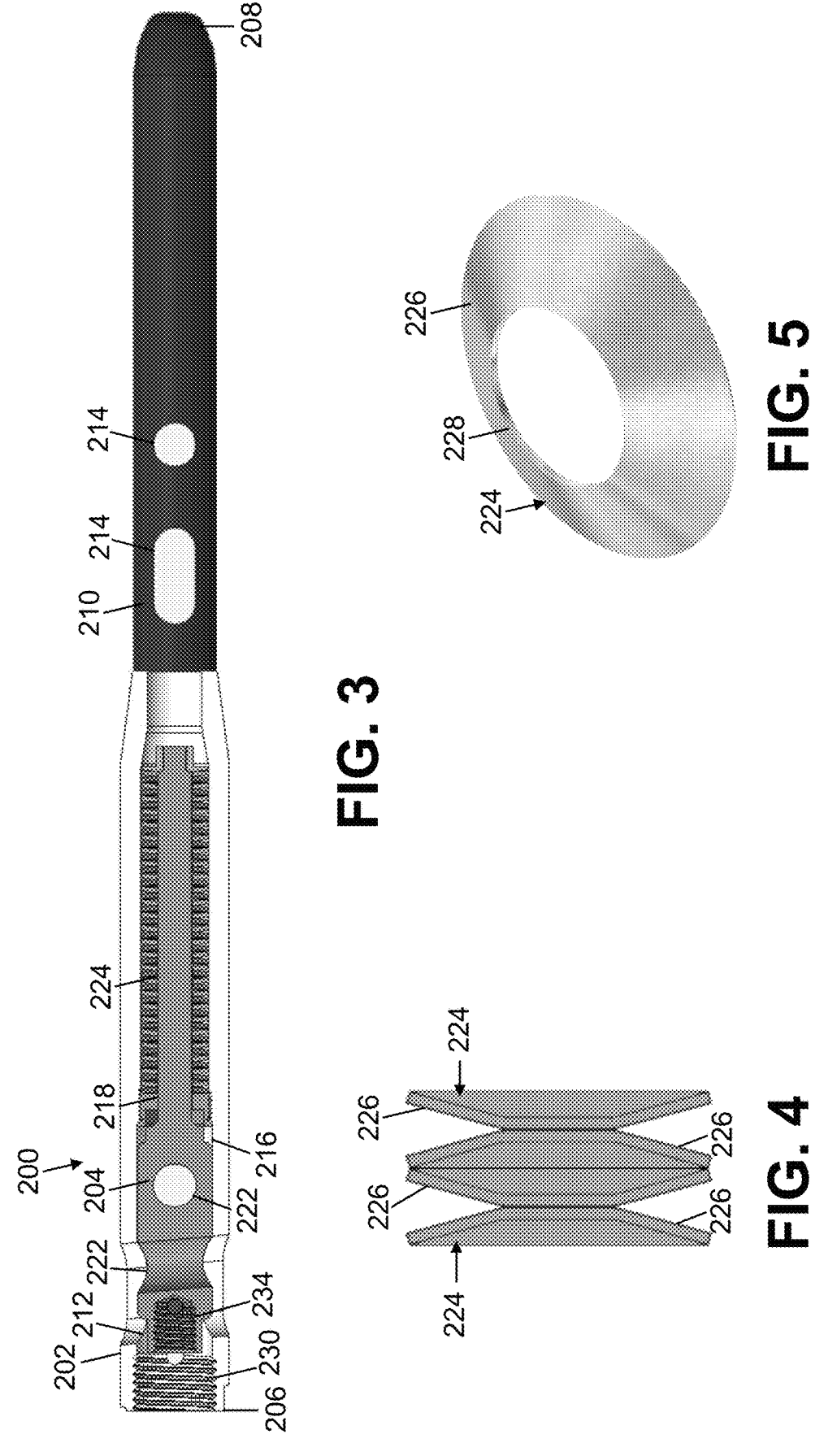
FIG. 3 is a partial sectional view of another example intramedullary nail.
FIG. 4 is a side view of elastic compression members stacked in an alternating configuration.
FIG. 5 is a perspective view of one of the elastic compression members illustrated in FIG. 4.
Figures 6, 7:
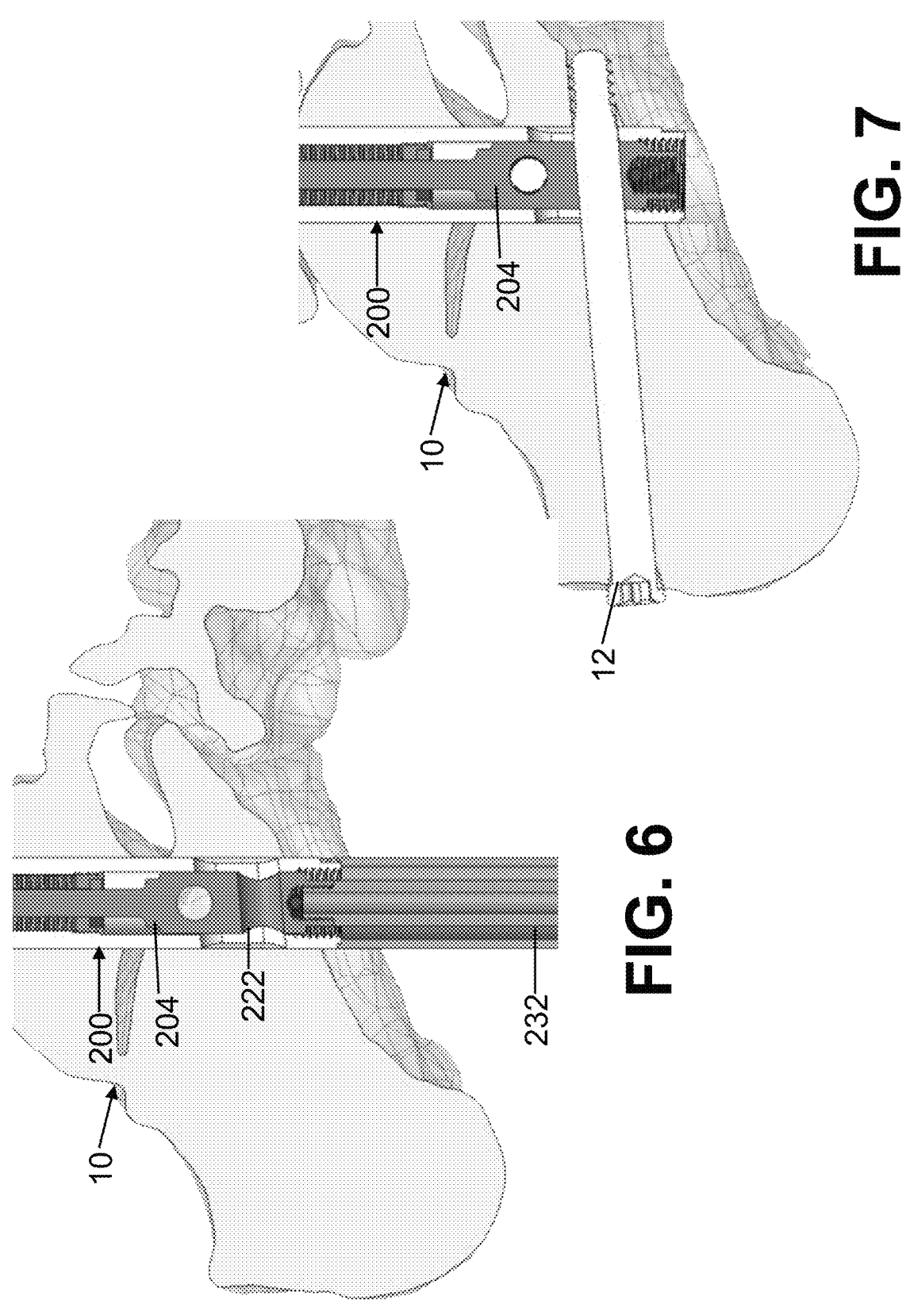
FIG. 6 is a sectional view of a human ankle with the intramedullary nail illustrated in FIG. 3 positioned in the human ankle. One end of the intramedullary nail is attached to a targeting device.
FIG. 7 is a sectional view of the human ankle with the intramedullary nail illustrated in FIG. 3 positioned in the human ankle. A screw is disposed through the intramedullary nail.

FIGS. 3, 6, and 7 illustrate another example intramedullary nail 200. The intramedullary nail 200 is similar to the intramedullary nail 100, except as described below. Thus, the intramedullary nail 200 has an elongate body 202, and a movable member 204. The elongate body 202 has a distal end 206, a proximal end 208, an outer surface 210, and an inner surface 212. The outer surface 210 and inner surface 212 can define one or more elongate body screw passageways 214 formed through the elongate body 202.

In this embodiment, the inner surface 212 defines a lumen 216 between the proximal end 208 and the distal end 206. The movable member 204 is disposed within the lumen 216. The movable member 204 has a movable member outer surface 218. The movable member 204 can also define one or more member screw passageways 220 formed through the movable member 204. The member screw passageway 220 can be adapted to align with one of the elongate body screw passageways 214 and receive a screw to restrict the movement of the movable member 204 by the length of the elongate body screw passageway 214.

In the illustrated example, the intramedullary nail 200 includes a peripheral projection, such as one or more elastic compression members 224, disposed around the movable member outer surface 218. The elastic compression members 224 function as the first peripheral projection 106 of the intramedullary nail 100. As such, elastic compression members 224 can be adapted to maintain a continuous compression force in the first direction. As shown in FIGS. 4 and 5, each of the elastic compression members 224 has a raised side 226 and an aperture 228 formed therethrough. The aperture 228 can be adapted to surround the movable member 204. The elastic compression members 224 are arranged in alternating orientations on the movable member outer surface 218. As shown in FIG. 4, the arrangement in alternating orientations can be defined as stacking pairs of the elastic compression members 224 together so that the raised sides 226 within each pair face each other. Desirably, the stack of the elastic compression members 224 in alternating orientations enables for greater deflection to maintain the compression force. Optionally the elastic compression members can be assembled in a multitude of orientations (alternating or in parallel) to achieve different compression forces and different deflection lengths. Each of the elastic compression members 224 can have a frustoconical shape. However, other shapes, such as a trapezoidal shape, may also be employed, within the scope of this disclosure. A non-limiting example of the elastic projection 224 includes a disc spring washer, as shown in FIG. 5. Advantageously, the disc spring washer provides sufficient force in a compact form factor. The compact nature of the spring washer can permit proximal screws to be lower in the tibia, which can optimize the location of the attaching cross screws into stronger bone. In other examples, the elastic compression members 224 can be substituted for a coil spring and an elastomeric polymer.

In the illustrated example, the distal end 206 of the elongate body 202 also has an elongate body threaded recess 230. The elongate body threaded recess 230 can be adapted to receive different attachments 232, such as a targeting jig, to assist in placing the intramedullary nail 200 into a bone. Likewise, a distal end-facing portion of the movable member 204 can include a movable member threaded recess 234. The movable member threaded recess 234 can be adapted to receive different attachments 232 to allow the movable member 204 to be manually moved to a compressive state within the lumen 216. FIGS. 6 and 7 illustrate the intramedullary nail 200 disposed within a human ankle 10. In FIG. 6, the attachment 232 is threadedly connected to the movable member threaded recess 234 to manually pull the movable member 204 down. Then in FIG. 7, a screw 12 is disposed through the movable member to lock the compression force in the first direction.

Figures 8, 9:
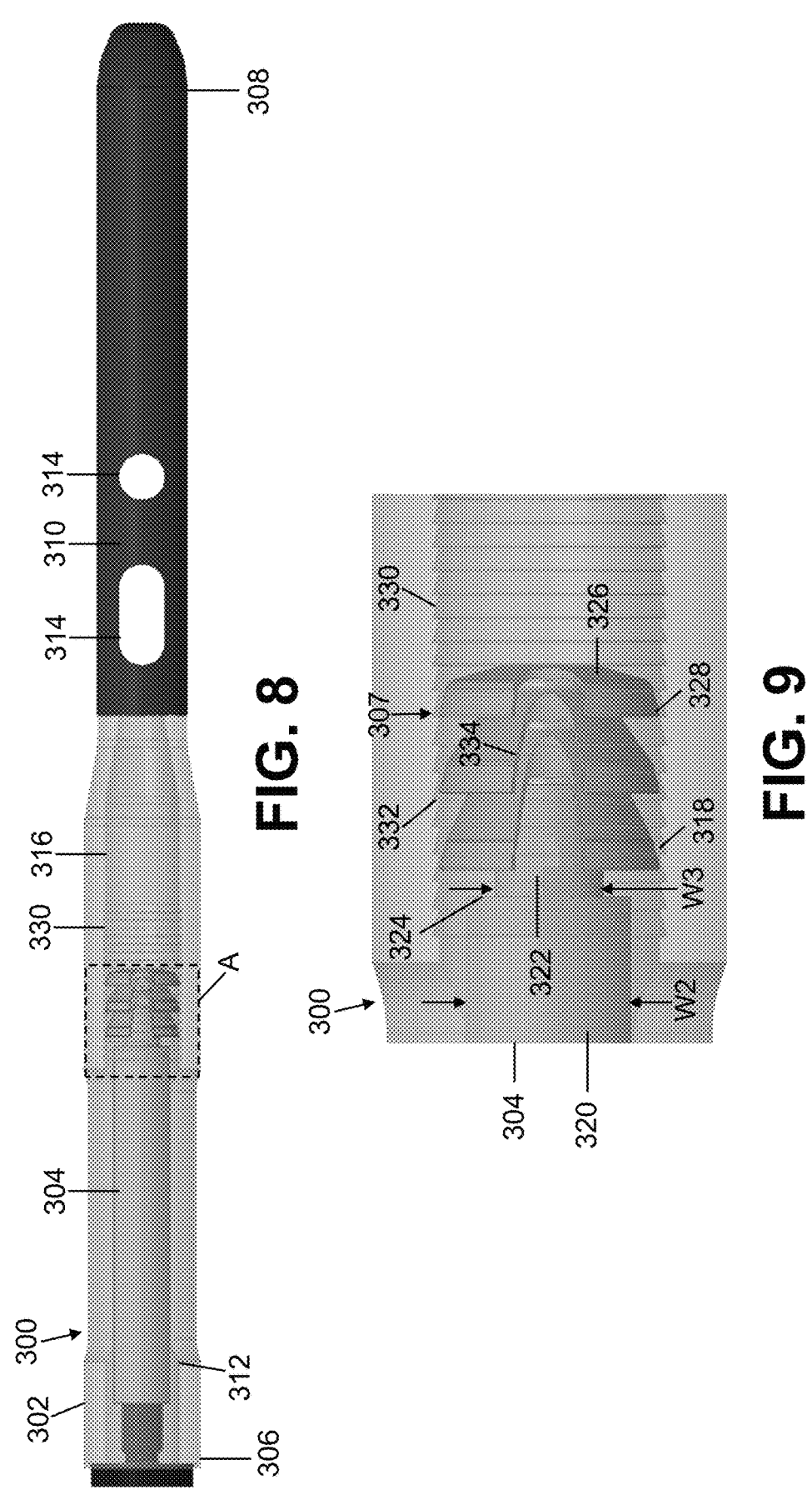
FIG. 8 is a partial sectional view of another example intramedullary nail.
FIG. 9 is an enlarged view of area A illustrated in FIG. 8 showing a moveable member inside the intramedullary nail. The inner surface of the intramedullary nail defines grooves.

FIGS. 8 and 9 illustrate another example intramedullary nail 300. The intramedullary nail 300 is similar to the intramedullary nail 100, except as described below. Thus, the intramedullary nail 300 has an elongate body 302 and a movable member, such as a movable member 304. The elongate body 302 has a distal end 306, a proximal end 308, an outer surface 310, and an inner surface 312. The outer surface 310 and the inner surface 312 can define one or more elongate body screw passageways 314 formed through the elongate body 302.

In this embodiment, the inner surface 312 defines a lumen 316 between the proximal end 308 and the distal end 306, and a receiving surface 307. The movable member 304 is disposed within the lumen 316. The movable member 304 includes a base portion 320 and an extension portion 322. The base portion 320 has a proximal facing edge 324. The extension portion 322 extends from the proximal facing edge 324 toward the proximal end 308b. The proximal facing edge 324 has a width W2 and the extension portion 322 has a width W3. The width W3 of the extension portion 322 is less than the width W2 of the proximal facing edge 324.

The extension portion 322 includes a peripheral projection, such as one or more discs 326. Each of the discs 326 include a flexible rim 328. The receiving surface 307 defines slanted grooves 318. Each of the slanted grooves 318 has a moderate groove slope 330 on one side of an edge and a steeper groove slope 332 on the other side of the edge. The moderate groove slope 330 faces the proximal end 308 while the steeper groove slope 332 faces the distal end 306. The flexible rim 328 can move substantially unrestricted toward the distal end 306 by traveling over the moderate groove slope 330. If a force attempts to move the flexible rim 328 back towards the distal end 306, the flexible rim 328 abuts against the steeper groove slope 332, thereby locking it against the steeper groove slope 332 and preventing motion towards the distal end 306. Each of the disc 326 can have a notch 334 formed within the disc 326 to facilitate the flexibility of the flexible rim 328. The notch 334 can be substantially u-shaped. In the illustrated example, the intramedullary nail 300 includes three discs 326. However, the intramedullary nail 300 can have more or less discs 326 depending on the amount of force the discs 326 must resist to militate against or prevent movement towards the distal end 306.

Figures 10, 11:
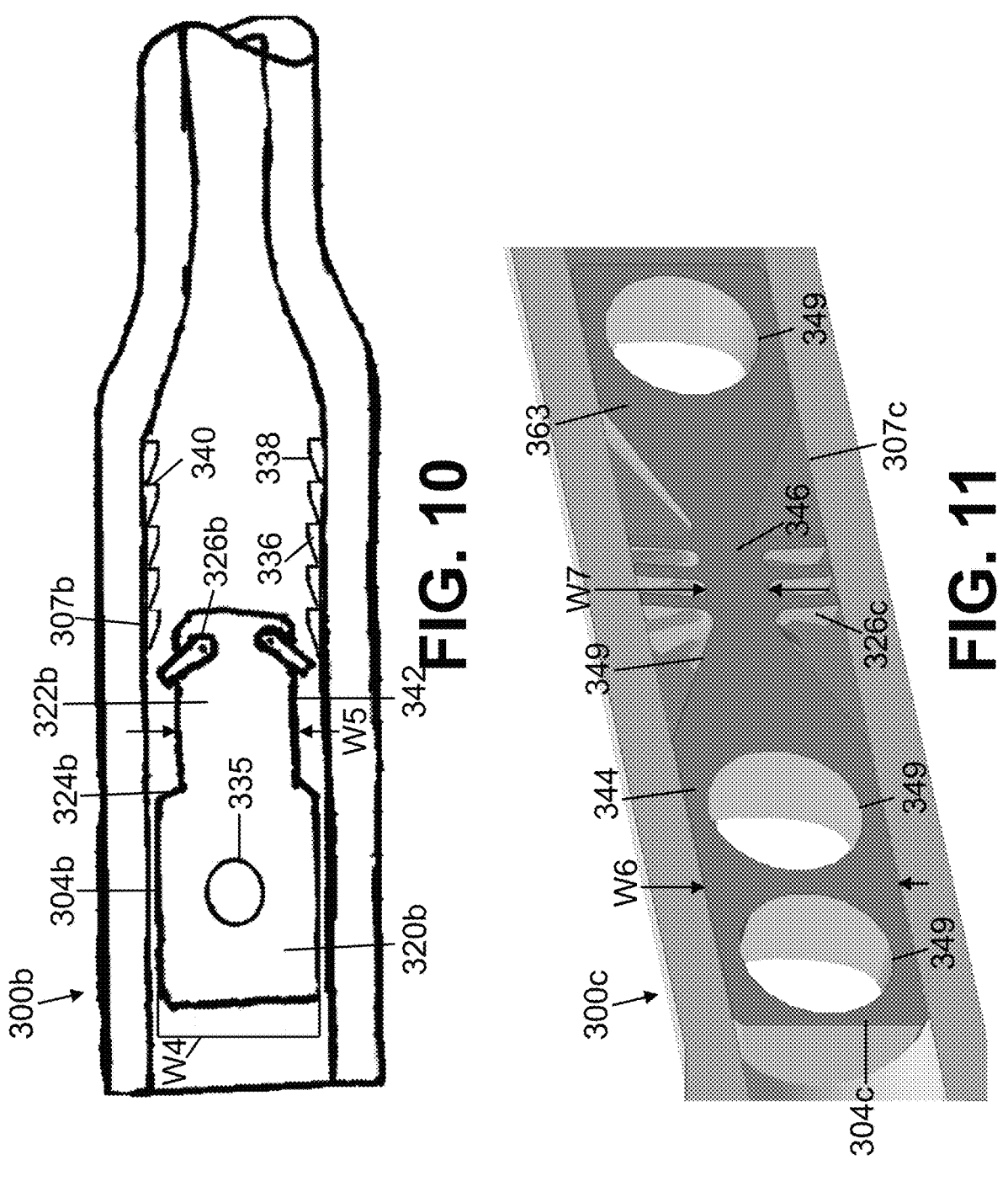
FIG. 10 is a sectional view of a portion of the intramedullary nail illustrated in FIG. 8 showing an alternative movable member inside the intramedullary nail. The inner surface of the intramedullary nail includes teeth.
FIG. 11 is a sectional view of a portion of the intramedullary nail illustrated in FIG. 8 showing an alternative movable member inside the intramedullary nail. The inner surface of the intramedullary nail is substantially smooth.

In an alternative example of intermammillary nail 300, shown in FIG. 10, an intramedullary nail 300b includes a movable member 304b. The movable member 304b includes a base portion 320b and an extension portion 322b. The base portion 320b can define one or more base screw passageways 335 formed through the base portion 320b. The base screw passageway 335 can be adapted to align with one of the elongate body screw passageways 314 and receive a screw to restrict the movement of the movable member 304b by the length of the elongate body screw passageway 314. The base portion 320b has a proximal facing edge 324b. The extension portion 322b extends from the proximal facing edge 324b toward the proximal end 308. The proximal facing edge 324b has a width W4 and the extension portion 322b has a width W5. The width W5 of the extension portion 322b is less than the width W4 of the proximal facing edge 324b. The extension portion 322b includes one or more ratcheting pawls 326b as the peripheral projection. A receiving surface 307b includes slanted teeth 336. The slanted teeth 336 can be disposed on the receiving surface 307b. Each of the slanted teeth 336 has a moderate tooth slope 338 on one side of an edge and a steeper tooth slope 340 on the other side of the edge. The moderate tooth slope 338 faces the distal end 306 while the steeper tooth slope 340 faces the proximal end 308. The ratcheting pawl 310a can move substantially unrestricted towards the proximal end 308 by traveling over the moderate tooth slope 338. If a force attempts to move the ratcheting pawl 310a back towards the distal end 306, the ratcheting pawl 310a abuts against the steeper tooth slope 340, thereby locking it against the steeper tooth slope 340 and preventing motion towards the distal end 306. In addition, the width W4 of the proximal facing edge 324b can be long enough to abut slanted teeth 336 after the extension portion 322b travels through receiving surface 307b. The ratcheting pawl 310a may be disposed on a teeth-facing side 342 of the movable member 304b and orientated away from the moderate tooth slope 338 of each of the slanted teeth 336. In the illustrated example shown in FIG. 10, there are two ratcheting pawls 326b. However, the number of the ratcheting pawls 326b can be changed based on how much force the ratcheting pawls 326b must resist to militate against or prevent movement in towards the distal end 306.

Figure 13:
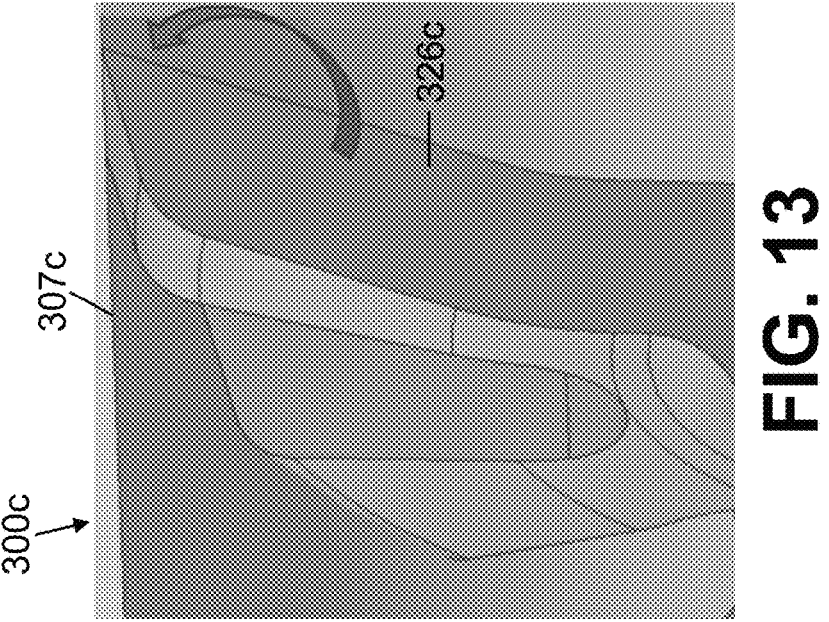
FIG. 13 is a perspective view of a portion of the intramedullary nail illustrated in FIG. 11 and showing the tine contacting an inner surface of the portion of the intramedullary nail in a second position.
Figure 12:
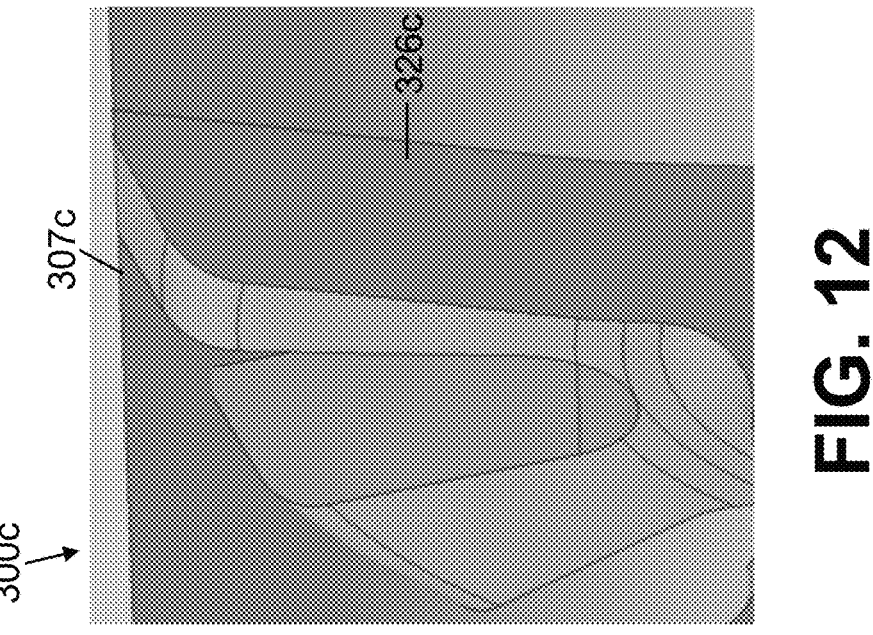
FIG. 12 is a perspective view of a portion of the intramedullary nail illustrated in FIG. 11 and showing a tine contacting an inner surface of the portion of the intramedullary nail in a first position.

In another alternative example of intermammillary nail 300, shown in FIG. 11, an intramedullary nail 300c includes a movable member 304c. The movable member 304c includes a first portion 344, an intermediate portion 346, and a second portion 348. The intermediate portion 346 is disposed between the first portion 344 and the second portion 348. Each of the first portion 344 and the second portion 348 can define one or more portion screw passageways 347 formed therethrough. The portion screw passageway 347 can be adapted to align with one of the elongate body screw passageways 314 and receive a screw to restrict the movement of the movable member 304c by the length of the elongate body screw passageway 314. Each of the first portion 344 and the second portion 348 can also have a width W6 and a slopped side 349 leading to the intermediate portion 346. The intermediate portion 346 can have a width W7. The width W7 can be less than the width W6. The intermediate portion 346 can have one or more tines 326c as the peripheral projection. A receiving surface 307c has a substantially smooth surface. When the tine 326c moves towards the proximal end 308, the tine 326c contacts the receiving surface 307c and bends, which induces a spring force (the bending is shown across FIGS. 12 and 13). If a force attempts to move the bent tine 326c back towards the distal end 306, the bent tine 326c with the spring force digs into the smooth surface of the receiving surface 307c to militate or prevent the movable member 304c from moving towards the distal end 306. The tine 326c can also have sharp edges to facilitate digging into the receiving surface 307c.

Figures 14, 15, 15A:
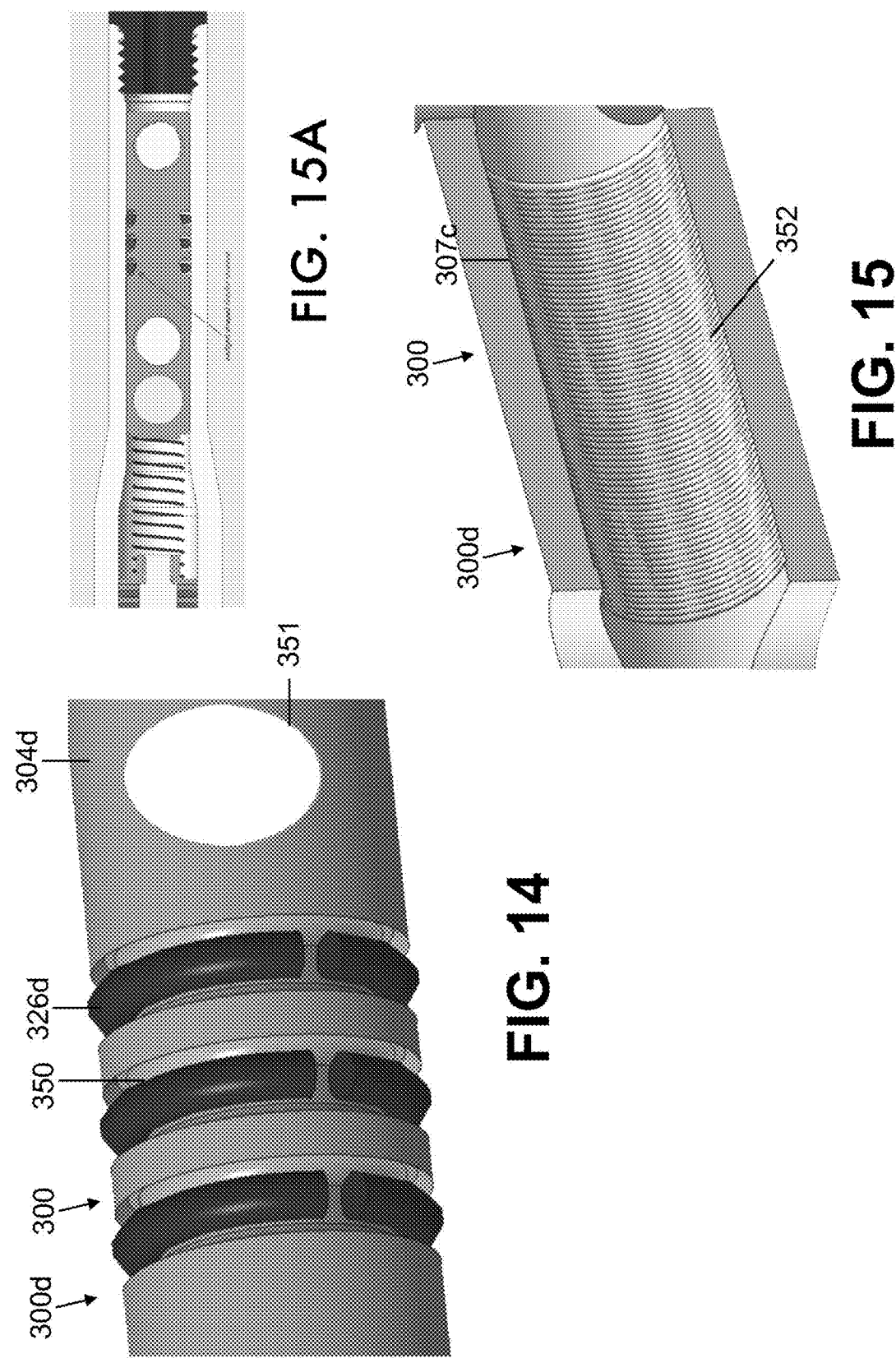
FIG. 14 is a partial perspective view of an alternative movable member of the intramedullary nail illustrated in FIG. 8 with split rings.
FIG. 15 is a partial perspective view of an alternative inner surface of the intramedullary nail illustrated in FIG. 8 defining stepped grooves.
FIG. 15A is a partial longitudinal sectional view of the intramedullary nail illustrated in FIG. 8 illustrating detail of the wedge-shaped circular channel.

In another alternative example of intermammillary nail 300, shown in FIGS. 14 and 15, an intramedullary nail 300d includes a movable member 304d. The movable member 304d has one or more split rings 326d as the as the peripheral projection. The movable member 304d can have one or more wedge shaped and circular channels 350 formed around the movable member 304d. Each of the wedge shaped and circular channels 350 receive one of the split rings 326d. The movable member 304d can define one or more member screw passageways 351 formed through the movable member 304d. The member screw passageway 351 can be adapted to align with one of the elongate body screw passageways 314 and receive a screw to restrict the movement of the movable member 304d by the length of the elongate body screw passageway 314. A receiving surface 307d includes stepped grooves 352. When split ring 326d moves toward the proximal end 308, the split ring 326d moves to a wider portion of the wedge shaped circular channel 350 and expands to fit the wider portion, thereby expanding against the grooves 352. If a force attempts to move the split ring 326d back towards the distal end 306, the now expanded split ring 326d abuts the wedge of the circular channel and prevents movement toward the distal end 306. In the illustrated example, the intramedullary nail 300d includes three split rings 326d. However, the intramedullary nail 300d can have more or less split rings 326d depending on the amount of force the split rings 326d must resist to militate against or prevent movement towards the distal end 306.

Figures 16, 17:
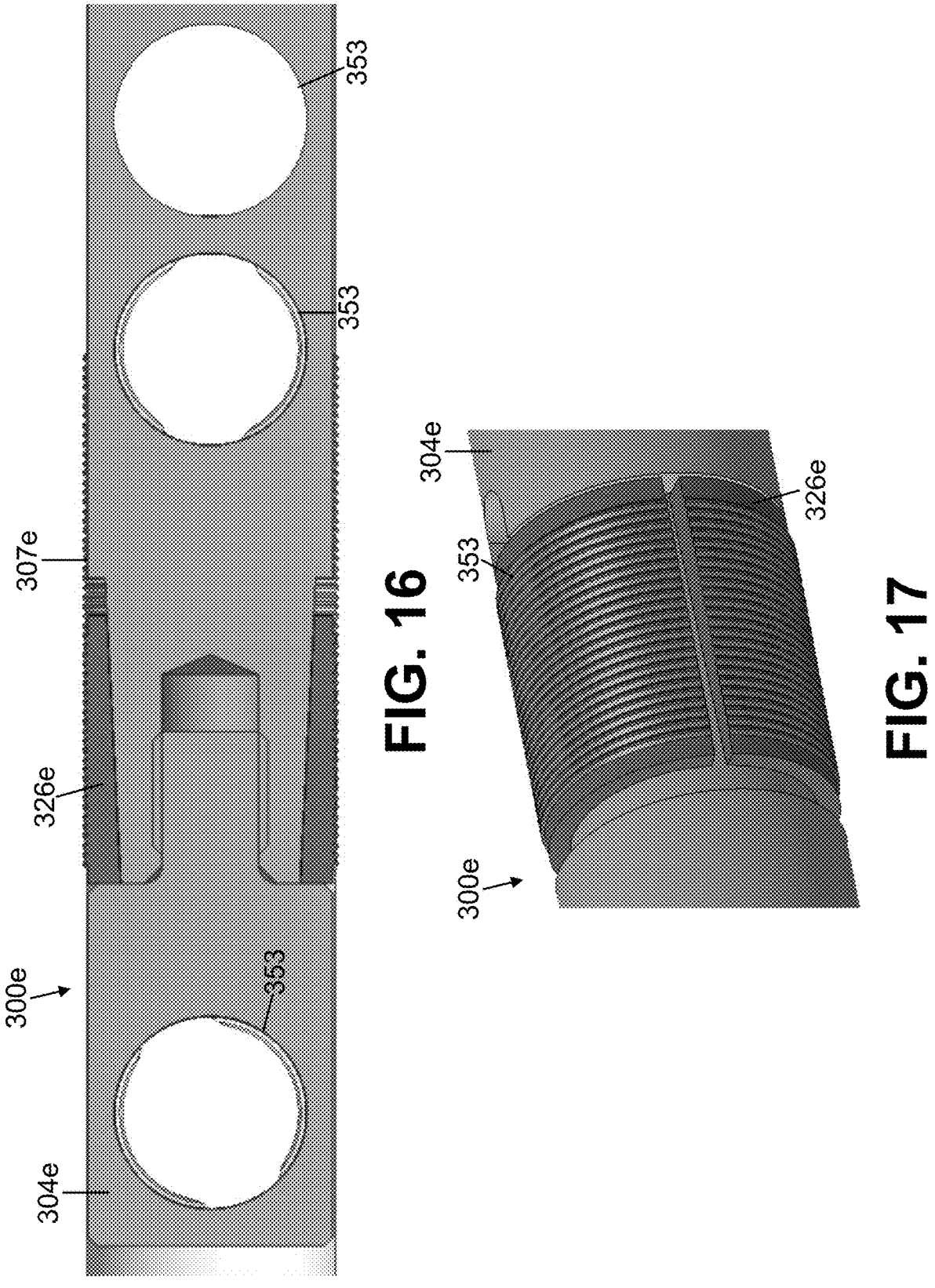
FIG. 16 is a sectional view of a portion of the intramedullary nail illustrated in FIG. 8 showing an alternative movable member inside the intramedullary nail with a wedged split ring sleeve. The inner surface of the intramedullary nail defines stepped grooves.
FIG. 17 is a partial perspective view of the alternative movable member of the intramedullary nail illustrated in FIG. 16 with the wedged split ring sleeve.
Figures 18, 19:
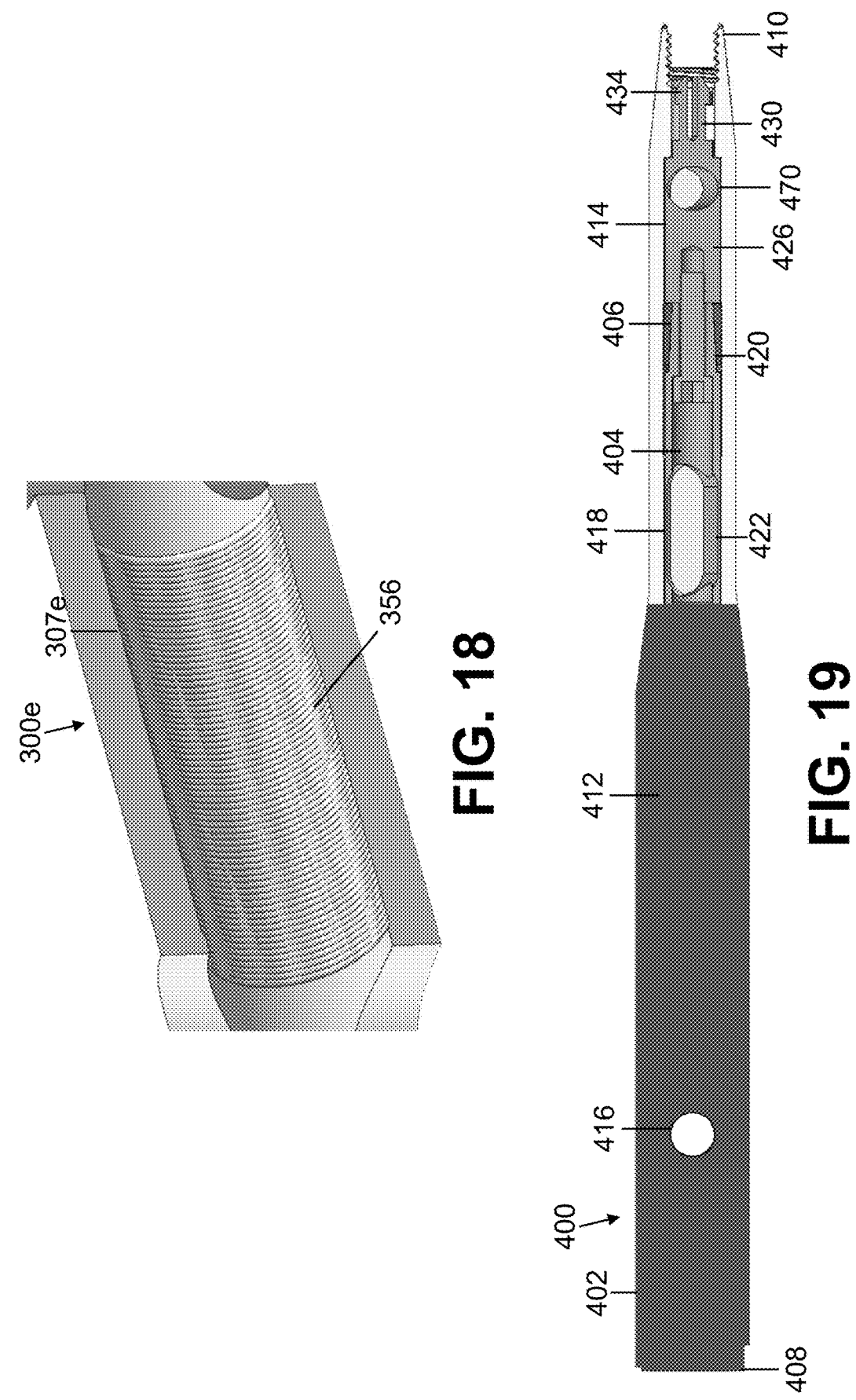
FIG. 18 is a partial perspective view of the inner surface of the intramedullary nail illustrated in FIG. 16 defining the stepped grooves.
FIG. 19 is a partial sectional view of another example intramedullary nail.
Figures 20, 21:
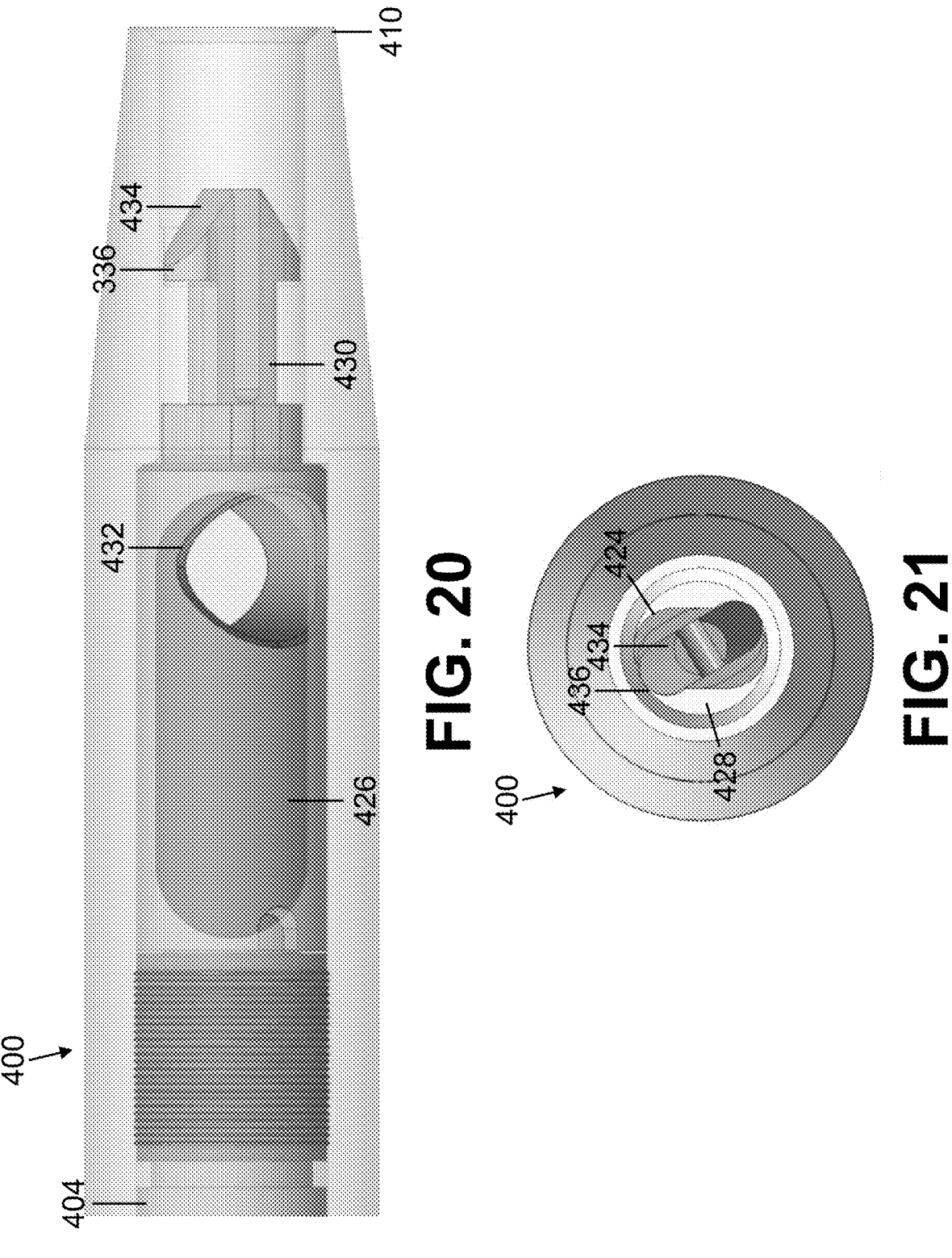
FIG. 20 is a partial sectional view of the locking portion of the intramedullary nail illustrated in FIG. 19. The locking portion is illustrated in a locked position.
FIG. 21 is an end view of the intramedullary nail illustrated in FIG. 19 and having the locking portion in a locked position.

In another alternative example of intermammillary nail 300, shown in FIGS. 16, 17, and 18, an intramedullary nail 300e includes a movable member 304e. The movable member 304e includes a wedged split sleeve 326e as the peripheral projection. The movable member 304e can define one or more member screw passageways 353 formed through the movable member 304d. The member screw passageway 353 can be adapted to align with one of the elongate body screw passageways 314 and receive a screw to restrict the movement of the movable member 304e by the length of the elongate body screw passageway 314. The wedged split sleeve 326e is disposed around the movable member 304e. The wedged split sleeve 326e has ridges 354 disposed on the wedged split sleeve 326e. A receiving surface 307e includes stepped grooves 356. When the movable member 304e moves toward the proximal end 308, the ridges 354 move to the wider grooves and expand to fit the wider grooves. If a force attempts to move the wedged split sleeve 326e back towards the distal end 306, the now expanded wedged split sleeve 326e abuts the narrower grooves and is prevented from moving towards the distal end 306. In the illustrated example, the movable member 304e includes two distinct portions joined together. However, it should be appreciated that the movable member 304e can be one integral piece.

FIGS. 19, 20, 21, 22, 23, and 24 illustrate another example intramedullary nail 400. The intramedullary nail 400 is similar to the intramedullary nail 100, except as described below. Thus, the intramedullary nail 400 has an elongate body 402, a movable member 404, and a peripheral projection 406. The elongate body 402 has a distal end 408, a proximal end 410, an outer surface 412, and an inner surface 414. The outer surface 412 and inner surface 414 can define one or more elongate body screw passageways 416 formed through the elongate body 402. The inner surface 414 defines a lumen 418 between the proximal end 410 and the distal end 408. The movable member 404 is disposed within the lumen 418. The movable member 404 has a movable member outer surface 420. The movable member 404 can also define one or more member screw passageways 422 formed through the movable member 404. The member screw passageway 422 can be adapted to align with one of the elongate body screw passageways 416 and receive a screw to restrict the movement of the movable member 404 by the length of the elongate body screw passageway 416.

In this embodiment, the proximal end 410 of the elongate body 402 includes a slot 424, and the movable member 404 includes a locking portion 426. The slot 424 is formed in the proximal end 410 of the elongate body 402. In the illustrated example, the proximal end 410 of the elongate body 402 includes a recess 428, and the slot 424 is formed in the recess 428. The locking portion 426 is disposed on a first direction-facing side of the movable member 404. The locking portion 426 includes one or more locking portion extensions 430 and one or more locking portion passageways 432. The locking portion passageway 432 is configured to selectively align with one of the elongate body screw passageways 416. The locking portion extension 430 is disposed on the locking portion 426 and extends toward the proximal end 410. The locking portion extension 430 includes a free end 434 having a ledge 436 extending from the free end 434. The ledge 436 is orientated orthogonal to the free end 434.

The locking portion 426 is adapted to move between a locked position and an unlocked position. In the locked position, shown in FIGS. 20 and 21, the ledge 436 of the locking portion extension 430 is disposed through the slot 424 and outside of the elongate body 402. The ledge 436 is misaligned with the slot 424 so that the ledge 436 is abutting a surface of the proximal end 410 of the elongate body 402. Since the locking portion 426 is connected to the movable member 404, the locked position militates against or prevents the movable member 404 from moving within the lumen 418. In certain examples, the ledge 436 is misaligned with the slot 424 by an angle between about 0 degrees to 90 degrees, between about 15 degrees to about 75 degrees, or about 30 degrees.

Figures 22, 23:
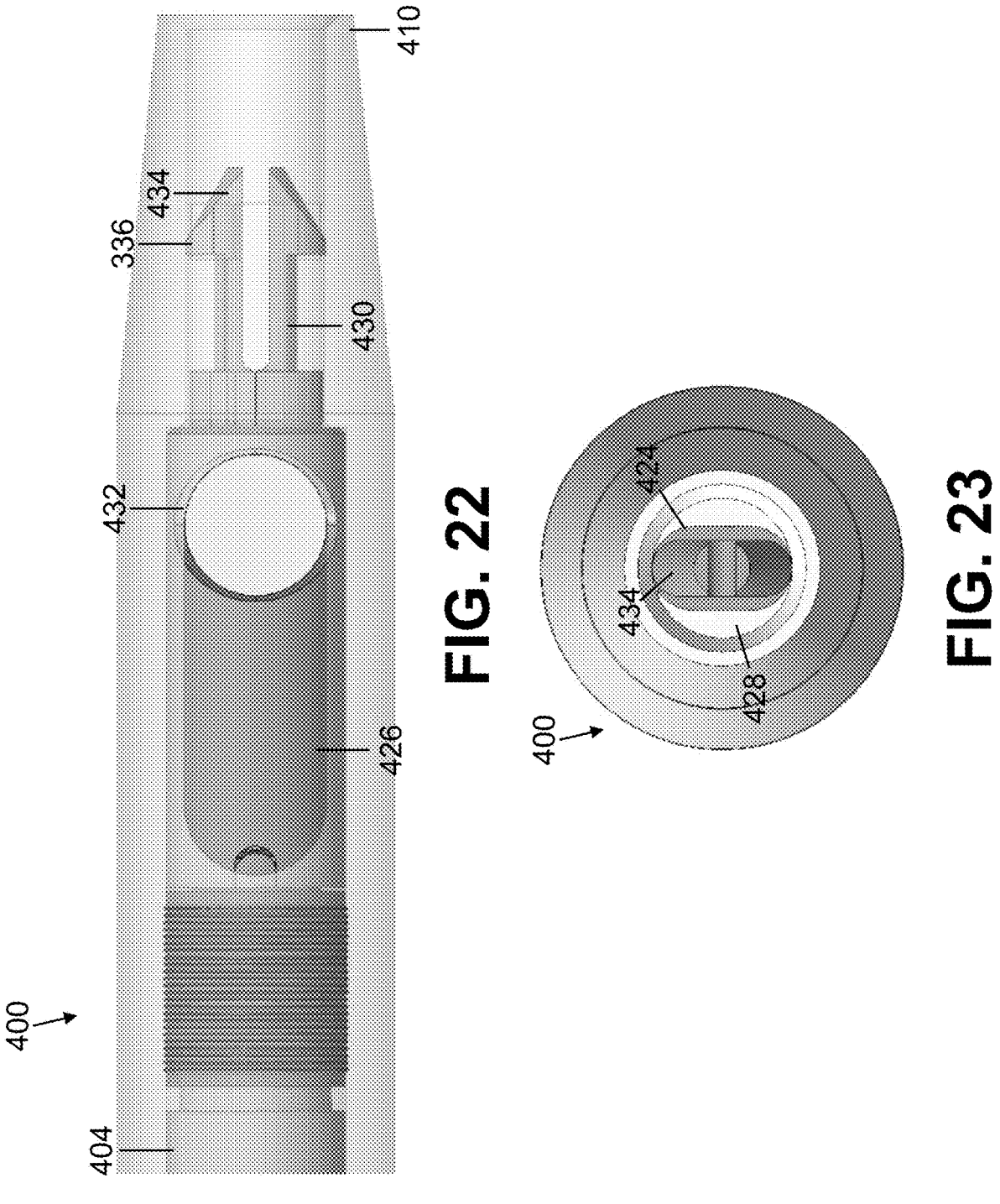
FIG. 22 is a partial sectional view of the locking portion of the intramedullary nail illustrated in FIG. 19. The locking portion is illustrated in an unlocked position.
FIG. 23 is an end view of the intramedullary nail illustrated in FIG. 19 and having the locking portion in an unlocked position.

In the unlocked position, shown in FIGS. 22 and 23, the ledge 436 is aligned with the slot 424 so that the ledge 436 is free to passthrough the slot 424, thereby allowing the movable member 404 to move within the lumen 418. The locked position can be advantageous for the initial implantation of the intramedullary nail 400 and for initial intraoperative compression. During the initial intraoperative compression, mallet impactions are used to compress the joint or fracture. The locked position can militate against or prevent unwanted movement of the movable member 404 during the initial intraoperative compression. This can be advantageous to prevent automatic dynamization from occurring while positioning the nail in the intramedullary canal. In certain examples, the locking portion 426 moves from the locked position to the unlocked position by inserting a screw through the locking portion passageway 432. The screwing action rotates the locking portion 426 so that the ledge 436 aligns with the slot 424.

In the illustrated example, the locking portion 426 includes two locking portion extensions 430 with the ledges 436. The two locking portion extensions 430 are spaced apart to provide a snapping latch when the locking portion 426 is in the locked position. However, it should be appreciated that the number of locking portion extensions 430 can be scaled, and other methods of selectively locking the movable member 404 can be employed within the scope of this disclosure.

Figures 24, 25:
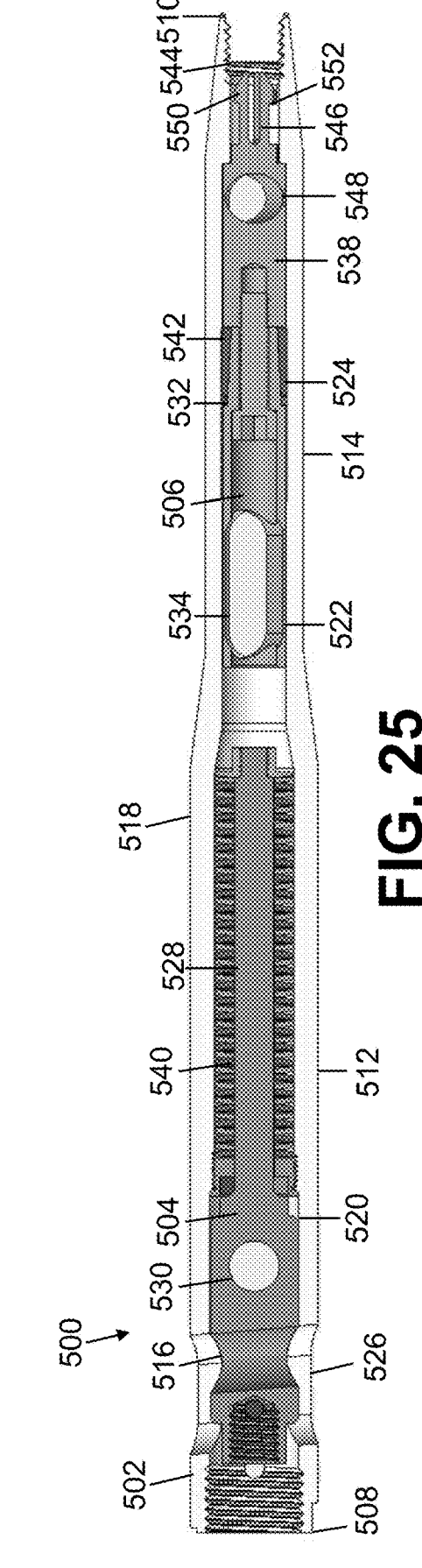
FIG. 24 is a section view of the proximal end of the intramedullary nail illustrated in FIG. 19. A proximal end cap is disposed on the proximal end of the intramedullary nail.
FIG. 25 is cross sectional view of another example intramedullary nail.
Figures 26, 27, 28:
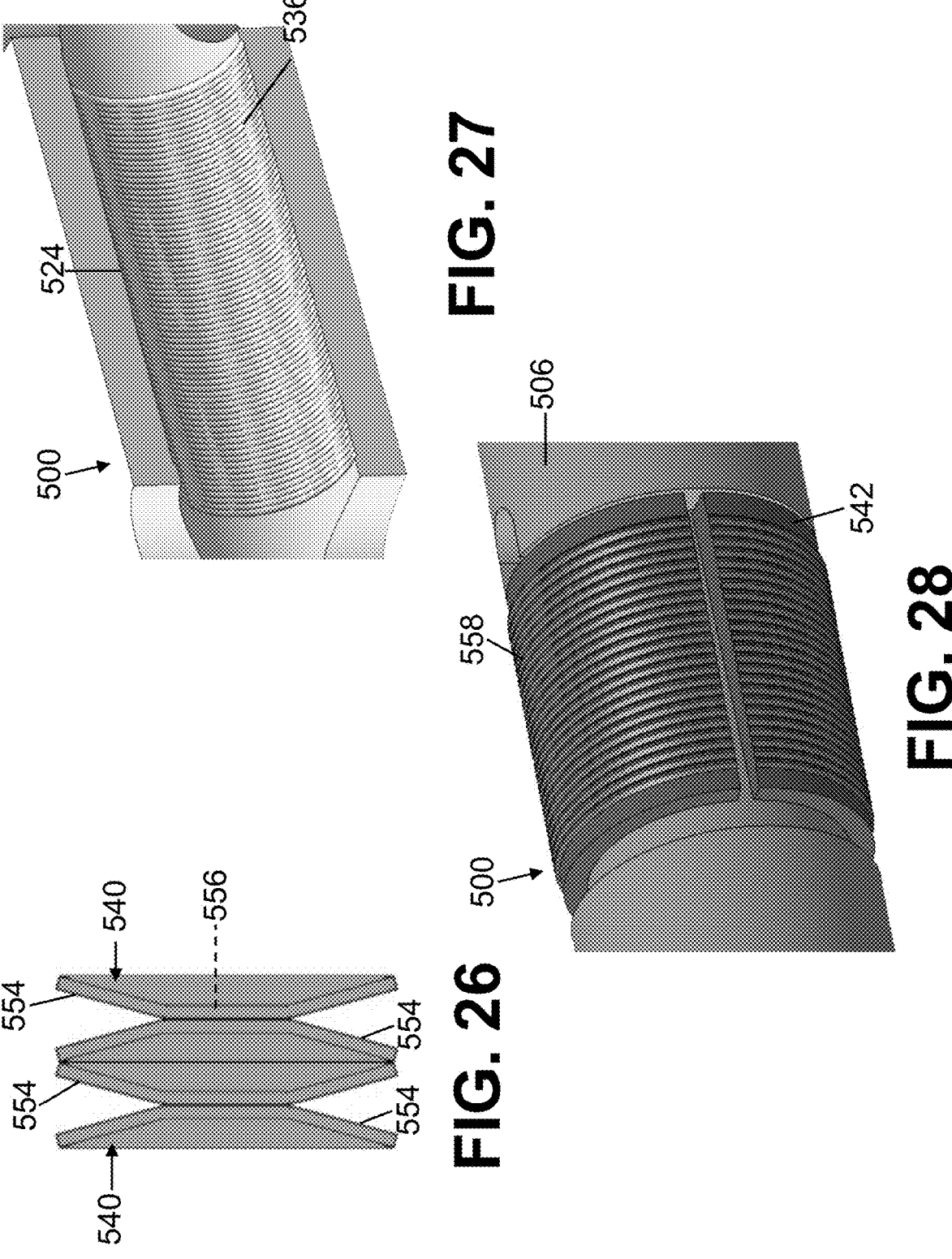
FIG. 26 is a side view of elastic compression members stacked in an alternating configuration.
FIG. 27 is a partial perspective view of the inner surface of the intramedullary nail illustrated in FIG. 25 defining stepped grooves.
FIG. 28 is a partial perspective view of the movable member of the intramedullary nail illustrated in FIG. 25 with the split ring sleeve.

In the illustrated example, shown in FIG. 24, the elongate body 402 further includes a proximal end cap 438. The proximal end cap 438 is disposed over the proximal end 410 of the elongate body 402. This can be desirable to cover the slot 424 formed in the proximal end 410 during implantation of the intramedullary nail 400. It should be appreciated that the locking portion 426 and the proximal cap 438 examples can also be used with the intramedullary nail 100 to achieve the same function. The end cap 438 is a purposeful modular member, which allows the inclusion of different end cpas of different lengths to be included with a particular intramedullary nail, allowing a clinician to customize one or more dimensions, such as an overall length, of the intramedullary nail to the anatomy of a particular patient. Indeed, a kit according to an embodiment includes an intramedullary nail according to an embodiment and two or more proximal end caps, each having a different axial length and all being configured to be disposed on the proximal end of the elongate body of the intramedullary nail of the kit. All of these components can be including in a single or multiple packages.

FIGS. 25, 26, 27, and 28 illustrate another example intramedullary nail 500. The intramedullary nail 500 is similar to the intramedullary nail 100, except as described below. Thus, the intramedullary nail 500 has an elongate body 502, a first movable member 504, and a second movable member 506. The elongate body 502 includes a distal end 508, a proximal end 510, a distal portion 512, a proximal portion 514, an inner surface 516, and an outer surface 518. The inner surface 516 defines a first lumen 520 extending through the distal portion 512, a second lumen 522 extending through the proximal portion 514, and a receiving surface 524. The outer surface 518 and inner surface 516 can define one or more elongate body screw passageways 526 formed through the elongate body 502. The first movable member 504 has a first movable member outer surface 528. The first movable member 504 can also define one or more first member screw passageways 530. The second movable member 506 has a second movable member outer surface 532. The second movable member 506 can also define one or more second member screw passageways 534.

In this embodiment, the receiving surface 524 includes stepped grooves 536; the second movable member 506 includes a locking portion 538; and the intramedullary nail 500 further comprises elastic compression members 540, a wedged split sleeve 542, and a slot 544. The stepped grooves 536 are similar or identical to the stepped grooves 356 of the intramedullary nail 300e. The locking portion 538 is similar or identical to the locking portion 426 of the intramedullary nail 400. Thus, the locking portion 538 includes an extension 546 and one or more locking portion passageways 548. The extension has a free end 550 with a ledge 552. The elastic compression members 540 are similar or identical to the elastic compression members 224 of the intramedullary nail 200. As such, the elastic compression members 540 are disposed on the first movable member outer surface 528. Each of the elastic compression members 540 has a raised side 554 and an aperture 556 formed therethrough. The elastic compression members 540 are arranged in alternating orientations. The wedged split sleeve 542 is similar or identical to the wedged split sleeve 326e of the intramedullary nail 300e. Thus, the wedged split sleeve 542 is disposed on the second movable member outer surface 532. The wedged split sleeve 542 has ridges 558. The slot 544 is similar or identical to the slot 424 of the intramedullary nail 400. Therefore, the slot 544 is formed in the proximal end 510 of the elongate body 502.

Advantageously, each of the intramedullary nails 100, 200, 300, 300b, 300c, 300d, 300e, 400, and 500 provide technical benefits over conventional intramedullary nails. The intramedullary nails 100, 500 can provide continuous compression and automatic dynamization to the fracture or fusion site. The intramedullary nail 200 can provide for at least continuous compression. The intramedullary nails 300, 300b, 300c, 300d, and 300e can provide for at least automatic dynamization. In addition, the intramedullary nails 400, 500 can provide for a one-way locking mechanism to selectively enable or disable for automatic dynamization.

Those with ordinary skill in the art will appreciate that various modifications and alternatives for the described and illustrated examples can be developed in light of the overall teachings of the disclosure, and that the various elements and features of one example described and illustrated herein can be combined with various elements and features of another example without departing from the scope of the invention. Accordingly, the particular examples disclosed herein have been selected by the inventors simply to describe and illustrate examples of the invention and are not intended to limit the scope of the invention or its protection, which is to be given the full breadth of the appended claims and any and all equivalents thereof.

We claim:

1. An intramedullary nail, comprising:
an elongate body having a distal end, a proximal end, a distal portion, a proximal portion, an inner surface, and an outer surface, the distal portion disposed between the distal end and the proximal portion, the proximal portion disposed between the distal portion and the proximal end, the inner surface defining a first lumen extending through the distal portion and a second lumen extending through the proximal portion, the inner surface including a receiving surface;
a first movable member disposed within the first lumen, the first movable member having a first movable member outer surface;
a plurality of members disposed on the first movable member outer surface, each member of the plurality of members having a raised side and the members of the plurality of members arranged in alternating orientations on the first movable member;
a second movable member disposed within the second lumen, the second movable member having a second movable member outer surface; and
a sleeve disposed on the second moveable member outer surface and about the second moveable member, the sleeve defining a longitudinal slit extending along an entire length of the sleeve.

2. The intramedullary nail of claim 1, wherein the receiving surface is a smooth surface.

3. The intramedullary nail of claim 1, wherein the receiving surface defines a plurality of slanted teeth.

4. The intramedullary nail of claim 1, wherein the receiving surface defines a plurality of grooves.

5. The intramedullary nail of claim 1, wherein the sleeve defines a plurality of ridges.

6. The intramedullary nail of claim 5, wherein the inner surface includes a second receiving surface defining a plurality of grooves disposed radially opposite the plurality of ridges.

7. The intramedullary nail of claim 1, wherein the second movable member includes a locking portion having an extension and a ledge.

8. The intramedullary nail of claim 7, wherein the proximal end defines a slot; and
wherein the locking portion is movable between a locked position in which the ledge is disposed through the slot and an unlocked position.

9. An intramedullary nail, comprising:
an elongate body having a distal end, a proximal end, a distal portion, a proximal portion, an inner surface, and an outer surface, the distal portion disposed between the distal end and the proximal portion, the proximal portion disposed between the distal portion and the proximal end, the inner surface defining a first lumen extending through the distal portion and a second lumen extending through the proximal portion, the inner surface including a receiving surface;
a first movable member disposed within the first lumen, the first movable member having a first movable member outer surface;

a plurality of elastic compression members disposed on the first movable member outer surface, each elastic compression member of the plurality of elastic compression members having a frustoconical shape and the elastic compression members of the plurality of elastic compression members arranged in alternating orientations on the first movable member;
a second movable member disposed within the second lumen, the second movable member having a second movable member outer surface; and
a sleeve disposed on the second moveable member outer surface and about the second moveable member;
wherein the sleeve defines a longitudinal slit.

10. The intramedullary nail of claim 9, wherein the sleeve defines a plurality of ridges.

11. The intramedullary nail of claim 10, wherein the inner surface includes a second receiving surface defining a plurality of grooves disposed radially opposite the plurality of ridges.

12. The intramedullary nail of claim 9, wherein the receiving surface is a smooth surface.

13. The intramedullary nail of claim 9, wherein the receiving surface defines a plurality of teeth.

14. The intramedullary nail of claim 9, wherein the receiving surface defines a plurality of grooves.

15. The intramedullary nail of claim 9, wherein the second movable member includes a locking portion having an extension and a ledge;
wherein the proximal end defines a slot; and
wherein the locking portion is movable between a locked position in which the ledge is disposed through the slot and an unlocked position.

16. An intramedullary nail, comprising:
an elongate body having a distal end, a proximal end defining a slot, a distal portion, a proximal portion, an inner surface, and an outer surface, the distal portion disposed between the distal end and the proximal portion, the proximal portion disposed between the distal portion and the proximal end, the inner surface defining a first lumen extending through the distal portion and a second lumen extending through the proximal portion, the inner surface including a first receiving surface comprising a smooth surface and a second receiving surface defining a plurality of grooves;
a first movable member disposed within the first lumen, the first movable member having a first movable member outer surface;
a plurality of elastic compression members disposed on the first movable member outer surface and radially opposite the first receiving surface, each elastic compression member of the plurality of elastic compression members having a frustoconical shape and the elastic compression members of the plurality of elastic compression members arranged in alternating orientations on the first movable member;
a second movable member disposed within the second lumen, the second movable member having a second movable member outer surface and a locking portion having an extension and a ledge and movable between a locked position in which the ledge is disposed through the slot and an unlocked position; and
a sleeve disposed on the second movable member outer surface and about the second movable member, the sleeve defining a longitudinal slit and a plurality of ridges disposed radially opposite the plurality of grooves defined by the second receiving surface.

* * * * *